(12) United States Patent
Orenstein et al.

(10) Patent No.: US 7,539,534 B2
(45) Date of Patent: May 26, 2009

(54) CONFIGURATION FOR PHONOGRAPHY CARDIO HEART MONITORING

(75) Inventors: Nicholas P. Orenstein, New York, NY (US); Ezra J. Rapoport, New York, NY (US)

(73) Assignee: Lono Medical Systems, LLC, Dallas, TX (US)

( * ) Notice: Subject to any disclaimer, the term of this patent is extended or adjusted under 35 U.S.C. 154(b) by 271 days.

(21) Appl. No.: 11/416,539

(22) Filed: May 2, 2006

(65) Prior Publication Data

US 2007/0270701 A1 Nov. 22, 2007

(51) Int. Cl.
*A61B 5/0448* (2006.01)

(52) U.S. Cl. ...................................................... 600/511
(58) Field of Classification Search .................. 600/511
See application file for complete search history.

(56) References Cited

U.S. PATENT DOCUMENTS

| | | | |
|---|---|---|---|
| 4,573,479 A | 3/1986 | Tuccillo | |
| 4,781,200 A * | 11/1988 | Baker | 600/483 |
| 4,898,179 A | 2/1990 | Sirota | |
| 4,947,859 A | 8/1990 | Brewer et al. | |
| 5,088,498 A | 2/1992 | Beach et al. | |
| 5,123,420 A | 6/1992 | Paret | |
| 5,140,992 A | 8/1992 | Zuckerwar et al. | |
| 5,365,937 A | 11/1994 | Reeves et al. | |
| 5,442,940 A * | 8/1995 | Secker et al. | 600/483 |
| 5,524,631 A | 6/1996 | Zahorian et al. | |
| 5,718,227 A | 2/1998 | Witlin et al. | |
| 5,807,271 A | 9/1998 | Tayebi et al. | |
| 5,885,222 A | 3/1999 | Kassal et al. | |
| 6,115,624 A * | 9/2000 | Lewis et al. | 600/376 |
| 6,236,862 B1 | 5/2001 | Erten et al. | |
| 6,245,025 B1 * | 6/2001 | Torok et al. | 600/500 |

(Continued)

FOREIGN PATENT DOCUMENTS

GB 2 162 644 A 2/1986

OTHER PUBLICATIONS

"Baby Bugging: Design of a miniature integrated fetal microphone," Dr. T.D. Rowsell, http://www2.eng.cam.ac.uk/-dmh/sig/hrm2.htm, pp. 1-5.

(Continued)

*Primary Examiner*—Mark W Bockelman
*Assistant Examiner*—Eric D Bertram
(74) *Attorney, Agent, or Firm*—Jones Day; Nicola A. Pisano, Esq.; Jamie D. Choi

(57) ABSTRACT

A method of acoustic monitoring includes transducing acoustic energy from a first acoustic transducer attached to a first location on a patient the acoustic energy from the first transducer, comprising desired acoustic energy to be monitored and interfering acoustic energy and transducing acoustic energy from a second acoustic transducer, attached to a second, different location on a patient, the acoustic energy from the second transducer, comprising desired acoustic energy to be monitored and interfering acoustic energy. The method also includes converting the acoustic energy sensed at the first and second locations into first and second electrical signals and processing the first and second electrical signals to digitally remove interfering acoustic energy present in the second signal to provide an electrical signal representative of the acoustic signal that is being monitored.

19 Claims, 16 Drawing Sheets

U.S. PATENT DOCUMENTS

| | | | |
|---|---|---|---|
| 6,454,716 | B1 | 9/2002 | Zumeris |
| 6,751,498 | B1* | 6/2004 | Greenberg et al. ........... 600/511 |
| 6,878,117 | B1 | 4/2005 | Watrous |
| 6,993,378 | B2 | 1/2006 | Wiederhold et al. |
| 7,022,077 | B2 | 4/2006 | Mourad et al. |
| 7,096,060 | B2 | 8/2006 | Arand et al. |
| 7,351,207 | B2 | 4/2008 | Priemer |
| 2001/0034490 | A1 | 10/2001 | Bryant et al. |
| 2002/0068874 | A1* | 6/2002 | Zuckerwar et al. ........... 600/511 |
| 2004/0073094 | A1 | 4/2004 | Baker |
| 2004/0102965 | A1 | 5/2004 | Rapoport |
| 2004/0243015 | A1 | 12/2004 | Smith et al. |
| 2004/0260188 | A1 | 12/2004 | Syed et al. |
| 2005/0113708 | A1 | 5/2005 | Priemer |
| 2005/0277841 | A1* | 12/2005 | Shennib ...................... 600/511 |
| 2007/0213627 | A1 | 9/2007 | James et al. |
| 2007/0260154 | A1 | 11/2007 | Rapoport et al. |
| 2007/0260155 | A1 | 11/2007 | Rapoport et al. |
| 2007/0276251 | A1 | 11/2007 | Orenstein et al. |

OTHER PUBLICATIONS

"Fetal Monitoring," Dr. T.D. Rowsell, http://www2.eng.cam.ac.uk/-dmh/sig/hrm3.htm, pp. 1-6.

"Measurement of compliance of the maternal abdominal wall in pregnancy," *Eur. J. Obstet. Gynecol. Reprod. Biol.*, 23 (1986) pp. 267-272.

"Fetal Monitoring," M.C. Carter, *J. Biomed. Eng.*, 1988, vol. 10, November, pp. 527-532.

"Wireless Fetal Heart Monitor," DRAFT, E. Rapoport, *Lono Acoustic Engineering*, Jun. 8, 2005.

"Development of a Fuzzy Rule-Based QRS Detection Algorithm for Fetal and Maternal Heart Rate Monitoring," *Proceedings of the 20th Annual Int'l Conf. of the IEEE Eng. In Medicine and Biol. Society*, vol. 20, No. 1, 1998, pp. 170-173.

"Linear and Nonlinear Parameters for the Analysis of Fetal Heart Rate Signal From Cardiotocographic Recordings," M. G. Signorini et al., *IEEE Transactions on Biomedical Engineering*, vol. 50, No. 3, Mar. 2003, pp. 365-374.

"Wide Bandwidth Fetal Phonography Using a Sensor Matched to the Compliance of the Mother's Abdominal Wall," D.G. Talbert et al., *IEEE Transactions on Biomedical Engineering*, vol. BME-33, No. 2, Feb. 1986, pp. 175-181.

"Metallized Piezo Film Sheets," *Measurement Specialties, Inc.*, May 2001, pp. 3-5.

"The Development of PC-Based Fetal Monitoring and Analysis System," S.I. Kim et al., *18th Annual Int'l Conf. of the IEEE Engineering in Medicine and Biol. Soc.*, Amsterdam 1996 1.1.1: Physiological Data Acquisition Systems, pp. 5-6.

"Development of a Piezopolymer Pressure Sensor for a Portable Fetal Heart Rate Monitor," A.J. Zuckerwar et al., *IEEE Transactions on Biomedical Engineering*, vol. 40, No. 9, Sep. 1993, pp. 963-969.

"Biophysical profile in the fetus from a phonographic sensor," N. Colley et al., *Eur. J. Obstet. Gynecol. Reprod. Biol.* 23 (1986), pp. 261-266.

"An experimental rig to simulate fetal heart sounds," D. Cohen et al., *Eur. J. Obstet. Gynecol. Reprod. Biol.* 23 (1986), pp. 273-280.

"Real Time Processing Algorithm for High Resolution Fetal Heart Rate Estimation," S. I. Kim et al., *IEEE Transactions* (1994), pp. 1288-1289.

"Real-Time Signal Processing for Fetal Heart Rate Monitoring," M.I. Ibrahimy, *IEEE Transactions on Biomedical Engineering*, vol. 50, No. 2, Feb. 2003, pp. 258-262.

"A Rule-Based Phonocardiographic Method for Long-Term Fetal Heart Rate Monitoring," F. Kovacs et al., *IEEE Transactions on Biomedical Engineering*, vol. 47, No. 1, Jan. 2000, pp. 124-130.

"A signal-processing research facility and its application to the processing of fetal phonocardiographic signals for heart rate estimation," J.H. Dripps et al., *Eur. J. Obstet. Gynecol. Reprod. Biol.*, 23 (1986), pp. 281-288.

"New Transducer for Detecting Fetal Heart Sounds: Use of Compliance Matching for Maximum Sound Transfer," D.G. Talbert et al., *The Lancet*, Feb. 25, 1984, pp. 426-427.

International Search Report for International Application No. PCT/US07/67906, Jul. 3, 2008 (3 pages).

* cited by examiner

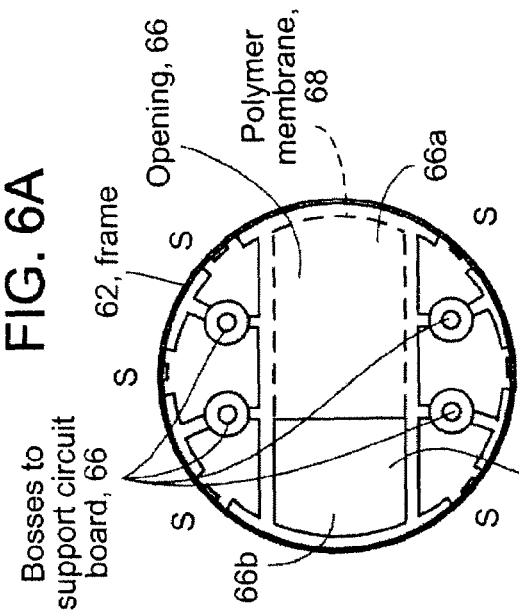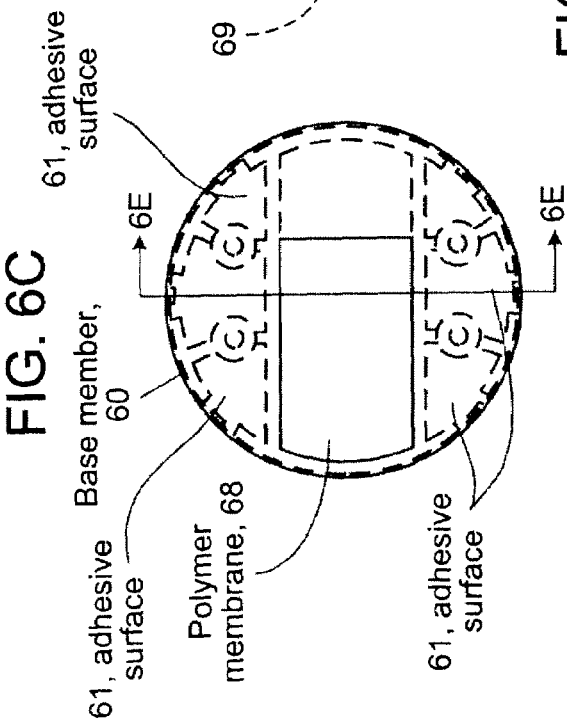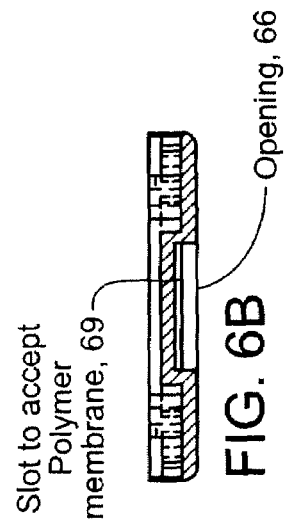

Dome cap, 80

Snap receptacle, 84

Binding posts

Snap receptacle aligned with base member, 84

CONFIGURATION FOR PHONOGRAPHY CARDIO HEART MONITORING

CROSS-REFERENCE TO RELATED APPLICATIONS

This application is related to the following U.S. patent applications:

U.S. patent application Ser. No. 11/417,038, filed May 2, 2006 and entitled "Passive Phonography Heart Monitor;"

U.S. patent application Ser. No. 11/417,315, filed May 2, 2006 and entitled "Transducers with Acoustic Impedance Matching for Passive Cardio Monitoring;" and U.S. patent application Ser. No. 11/416,885, filed May 2, 2006 and entitled "Fetal Heart Monitoring."

BACKGROUND

This invention relates to detecting acoustic energy and in particular fetal heart monitoring.

Fetal heart monitoring is a diagnostic tool to indicate the overall health status of a fetus. Currently deployed fetal heart monitoring techniques are primarily ultrasound, Doppler-based. With a typical ultrasound Doppler-based technique, wires are deployed between an ultra sound transducer unit and processing unit. A skilled operator, such as a medical technician or nurse scans or places a transceiver on the abdomen of the patient. Typically, the operator covers a region on the abdomen with a gel and moves the ultrasonic sensor around the area to scan the area. Alternatively, the sensor can be affixed with a belt that is worn around the woman. The belt is cumbersome and inaccurate (often the sensor slips off of its target) and it has to be removed prior to any surgery or emergency procedure. Acoustic signals are emitted from the transducers and their echo signals are detected by the transceiver and processed to produce data pertaining to the fetal heart rate.

Current Doppler-based techniques for fetal monitoring have several limitations. One limitation of current Doppler-based techniques is the lack of specificity for detecting fetal heart tones (FHT's). In cases of maternal tachycardia, the operator may not be able to differentiate whether the transducer is detecting the fetal or maternal signal, and this can have catastrophic consequences.

Other limitations pertain to changes in fetal position or station which often require re-positioning of the transducer, which can be time-consuming and result in "blackout" periods in fetal monitoring, during which medical personnel do not receive data from monitors that monitor the fetus. Another limitation is the loss of continuous monitoring in a distressed fetus, especially during transition periods, e.g., moving from a delivery room to an operating room for an emergency Cesarean section procedure. In addition, many hospital protocols require detachment of all wires from fetal monitoring devices during room transfers. Detaching fetal monitors begins another "blackout period."

Administration of epidural anesthesia presents another potential "blackout" period for fetal monitoring, as the transducer is frequently removed or displaced during that procedure. This, too, is a critical time frame for fetal monitoring, as epidural anesthesia may cause maternal hypotension with subsequent fetal bradycardia.

Maternal ambulation has been shown to facilitate labor progress, but current techniques typically preclude such standing deliveries.

A newer monitoring technique known as fetal phonography uses a passive acoustic sensor to capture acoustic energy from the maternal abdomen. Typically, the sensor includes a piezoelectric element. In a paper entitled "*Development of a Piezopolymer Pressure Sensor for a Portable Fetal Heart Rate Monitor*" by Allan J. Zuckenvar et al., IEEE TRANSACTIONS ON BIOMEDICAL ENGINEERING. VOL. 40, NO. 9. SEPTEMBER 1993 p. 963, the authors described a pressure sensor array mounted on a belt worn by the mother. The sensor array uses two polyvinyldene fluoride elements arranged in a bimorph structure, mechanically in series and electrically in parallel.

SUMMARY

According to an aspect of the present invention, a method of acoustic monitoring includes transducing acoustic energy from a first acoustic transducer attached to a first location on a patient the acoustic energy from the first transducer, comprising desired acoustic energy to be monitored and interfering acoustic energy, transducing acoustic energy from a second acoustic transducer, attached to a second, different location on a patient, the acoustic energy from the second transducer, comprising desired acoustic energy to be monitored and interfering acoustic energy, converting the acoustic energy sensed at the first and second locations into first and second electrical signals and processing the first and second electrical signals to digitally remove interfering acoustic energy present in the second signal to provide an electrical signal representative of the acoustic signal that is being monitored.

The following are embodiments within the scope of the invention.

The interfering acoustic energy is principally representative of a maternal heartbeat. The acoustic energy to be monitored includes acoustic energy representative of a fetal heartbeat and processing the first and second electrical signals provides the electrical signal representative of the fetal heartbeat. The method includes transducing a plurality of signals from a plurality of transducers, including the first transducer, the plurality of signals representing the acoustic energy to be monitored and processing the first the plurality of signals along with the second electrical signal to provide the electrical signal representative of the acoustic energy to be monitored. The acoustic energy to be monitored includes acoustic energy representative of a fetal heartbeat and processing the plurality of signals including the first signal, and second electrical signals provides the electrical signal representative of the fetal heartbeat.

According to an aspect of the present invention, a method of monitoring health status of a fetus includes transducing acoustic energy from a first acoustic transducer attached to the epidermis about the vicinity of the abdomen of a pregnant woman, the acoustic energy from the first transducer, comprising acoustic energy of a fetal heartbeat and interfering acoustic energy of a maternal heartbeat, transducing acoustic energy from a second acoustic transducer, attached to the percordium region of a pregnant woman, the acoustic energy from the first transducer the acoustic energy from the second transducer, comprising the interfering acoustic energy of the maternal heartbeat, converting the acoustic energy sensed at the first and second locations into first and second electrical signals and processing the first and second electrical signals to provide an output signal representative of the fetal heartbeat.

The interfering acoustic energy is removed during processing of the first and second signals. The processing includes processing at least the second electrical signal to provide a second output signal representative of the maternal heartbeat.

The second transducer is attached beneath the percordium area of the patient. The method includes converting acoustic energy representative of maternal uterine contractions into a third electrical signal. The method includes processing the third electrical signal to provide a signal representative of a rate of maternal uterine contractions. The method is applied to monitor fetal heartbeats and includes attaching the first transducer to the abdominal region of the patient in a region where the back of the fetus is against the maternal abdominal wall.

The method includes rendering the electrical signal representative of the fetal heartbeat on an output device. The output device is an audio speaker. The output device is a display device that renders an electrocardiogram. The output device is a display device that renders readout of heartbeat rate. The method includes rendering the second output signal representative of the maternal heartbeat on an output device. The acoustic transducers are wireless. The acoustic transducers are coupled to a processing device via cables and/or wires.

One or more aspects of the invention may provide one or more of the following advantages.

The monitor is capable of functioning without a skilled technician being present. Additionally, the monitor can be relatively low in cost compared to currently employed ultrasound based monitors by avoiding need for relatively expensive crystals commonly employed in the ultrasound transducers. The monitor uses low-cost sensing, transmission, and circuitry components suitable for operation in hospitals, physician offices, or home.

The monitor uses transducer sensor units that are disposable. The disposable nature of the transducer sensor units enables the monitor to ensure a very high standard of accuracy for these transducer sensor units because the term of use for each transducer sensor unit will not exceed a specified time duration. Hence, normal concerns of quality degradation resulting from extended use are avoided, while maintaining a relatively high level of performance. The monitor avoids blackout periods, e.g., the potentially most dangerous window of time during labor since the monitor in the wired and especially the wireless form allows for constant monitoring. Accurate, wireless monitoring system aids in decreasing labor time by increasing the potential mobility of the patient, thus making the resources in a labor-and-delivery unit more available.

The monitor uses a pitch period detector and a principal component analyzer to analyze signals from the sensors. This permits sophisticated and accurate fetal signal processing to be employed in the monitor at a relatively low cost. The monitor allows for maternal ambulation during labor, providing a number of potential benefits.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 6A-6E-8A-8C (collectively, FIGS. 6-8) are diagrams depicting construction details of sensors used with the monitor of FIG. 3.

DETAILED DESCRIPTION

Figure 1:
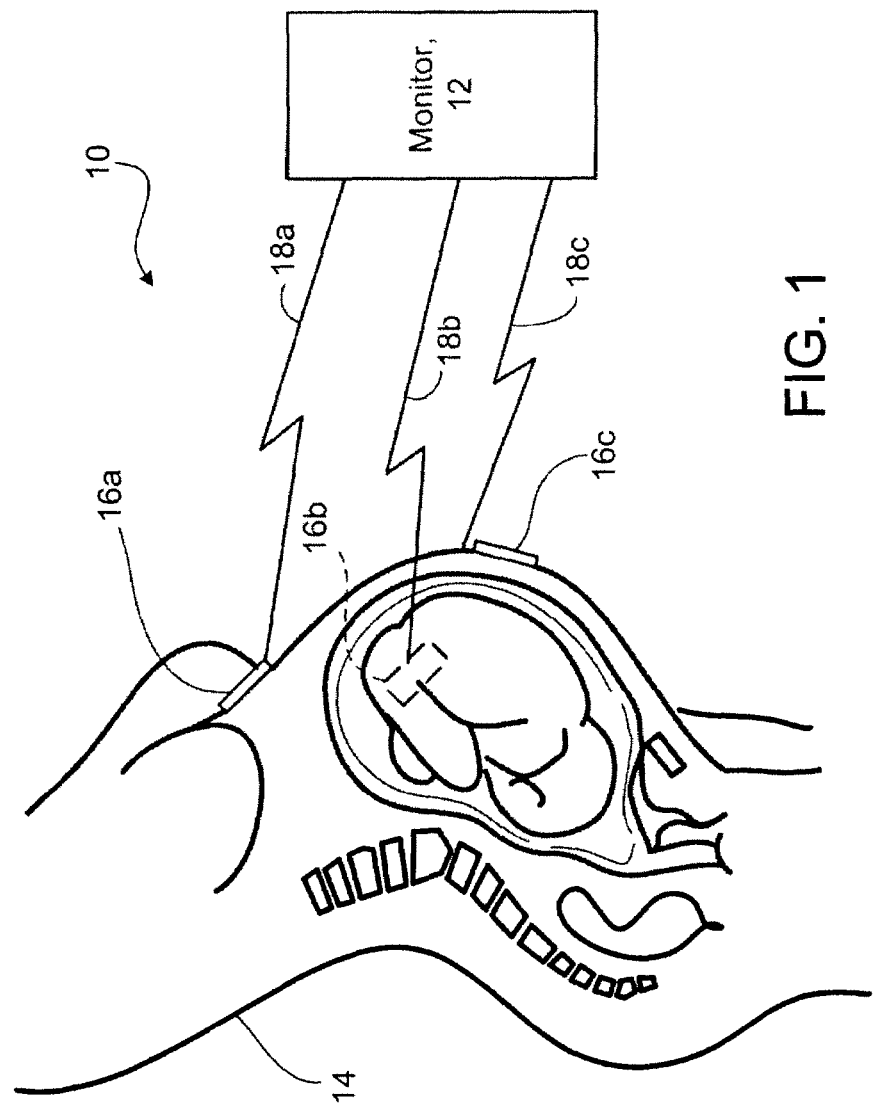
FIG. 1 is a block diagram of a monitoring scheme.

Referring to FIG. 1, an arrangement 10 for connection of a monitor device 12 ("monitor") to a patient, e.g., pregnant woman 14 to monitor fetal heartbeat signals is shown. The monitor 12 can be used for various types of monitoring, as discussed below. In this example, the monitor 12 is a fetal heartbeat monitor.

The monitor 12 (discussed in detail below) has acoustic transducer (sensors) 16a-16c that convert acoustic energy from the pregnant woman 14 into electrical energy. The transducers 16a-16c are coupled to the monitor 12, via communication channels, 18a-18c, which can be wires connecting to the monitor 12 or wireless channels (radio frequency, optical and/or infrared). In one embodiment, Bluetooth® wireless technology is used.

In one configuration for connection of the monitor 12 to the patient, one of the transducers, e.g., transducer 16a monitors the pregnant woman's heartbeat, another one of the transducers 16b monitors the pregnant woman's uterus to measure uterine contractions. The transducer to monitor the uterine contractions, is not essential to capturing the fetal heartbeat but is included as part of an overall tool to monitor the health and status of the patient and fetus. The third transducer 16c monitors the fetal heartbeat. The location of the pregnant woman's heart and uterus are readily predictable. The acoustic energy from the fetal heart is omni-directional but localized about the back of the fetus. Such localization is attributed to preferred acoustic propagation to sites where the fetal back is against the maternal abdominal wall. The acoustic propagation through the maternal wall is omni-directional but there is a point of maximum acoustic conduction, which is the point where the fetus, back is pressed against the uterine wall. However, other positions can be used to attach the transducer 16c to the pregnant woman.

In another configuration for connection of the monitor 12 to the patient, transducer 16a is arranged to monitor the pregnant woman's heartbeat and transducers 16b monitors the pregnant woman's uterus to measure uterine contractions. To capture fetal acoustic energy, a plurality of transducers (not shown) 16c can be deployed to monitor the fetal heartbeat. The multiple acoustic transducer 16c are deployed for fetal detection and arranged about the maximal fetal acoustic energy. This is a noise reduction technique that can be used in cases where it is difficult to sense the fetal heartbeat (e.g., in the case of an overweight pregnant woman or underweight fetus) extra fetal sensors can be deployed to boost the strength of the fetal signal. Furthermore, 3 or more fetal sensors can be used to triangulate the position of the fetal heart. This localization information can be used by doctors and technicians during labor and delivery.

Figure 2:
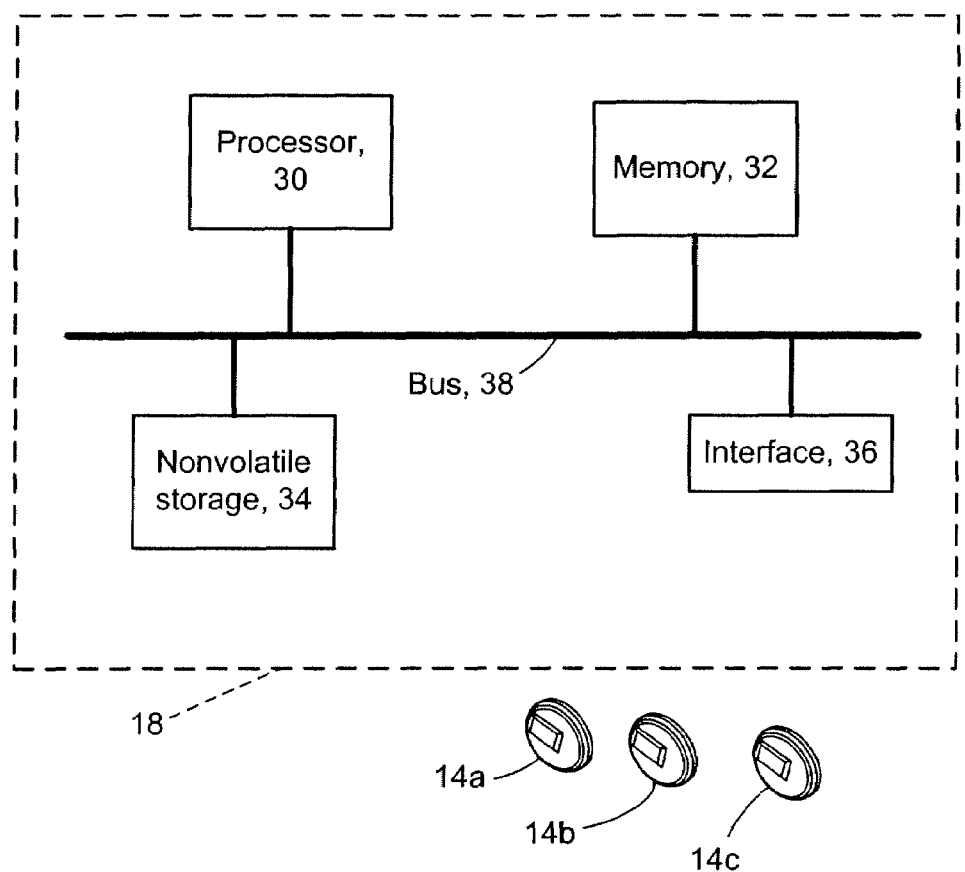
FIG. 2 is a block diagram of fetal monitor device used to monitor fetal cardiac activity.

Referring to FIG. 2, the monitor 12 includes a processor 30, e.g., a general purpose central processing unit (CPU) and/or a digital signal processor (DSP) to process signals from the patient, a memory 32, to execute programs, persistent, e.g., non-volatile storage 34, and I/O interface(s) 36 all coupled via a bus 38. Executed by the monitor 12 is signal processing software 50 that processes ECG signals detected by transducers 14a and 14c from the pregnant woman's heart and the fetus's heart, respectively. The monitor 12 also processes signals from the transducer 14b that monitors for contractions in the pregnant woman's uterus.

Processing 50 provides a relatively clean detection of the fetal heartbeat by eliminating major sources of noise in the fetal heartbeat signal, e.g., the relatively strong acoustic energy components contributed to the detected fetal heartbeat caused by the pregnant woman's heartbeat. In some embodiments, acoustic energy components from uterine contractions could also be filtered from the detected fetal heartbeat acoustic energy, but in general that is an insignificant contributor to noise in detection of the fetal heartbeat.

The monitor 10 can also include other user interface devices, e.g., keyboard or keypad, a display, speakers, headphone, etc. (not shown). In addition, the monitor can include a transmission channel to upload data to a server or the like.

Figure 3:
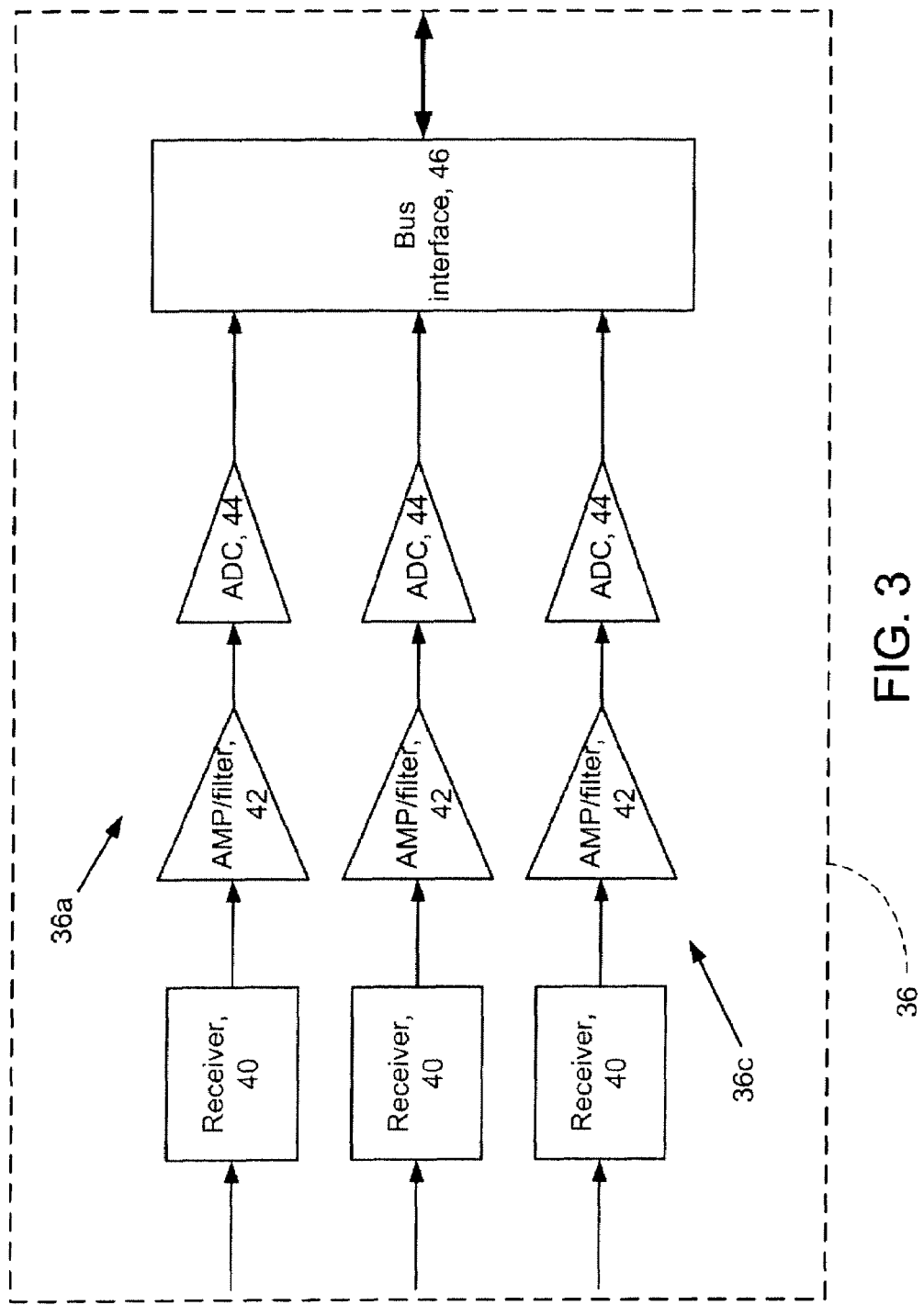
FIG. 3 is a flow chart depicting aspects of processing in the fetal monitoring device of FIG. 2.

Referring to FIG. 3, the monitor 12 includes an interface 36 that interfaces the monitor 12 to the transducers 16a-16c. The interface 36 here is shown to include channels 36a-36c for transducers 16a-16c, respectively. Each channel 36a-36c includes a receiver 40 (if the monitor is a wireless version) or an analog signal interface (not shown) to cables (not shown) from the transducer, if the monitor 12 is a wire-connected version. In addition, the interface 36 includes a low noise amplifier and a filter generally 42 to process analog signals from the transducers 16a-16c.

The amplifier 14 amplifies the signals and the filter filters the signals to preserve frequencies in the range of, e.g., 0.05 to 100 Hz or so. Typically, the fetal channel in the monitor 12 can be within the broad range above, but most likely will in a range about 10 to 30 Hz and especially in a range of 18 to 25 Hz (the range of maximal spectral power of the fetal heart signal). The maternal channel can be within the broad range above, but most likely will in a range about 6 to 14 Hz and especially in a range of 8 to 12 Hz (the region of maximal power of the maternal heart signal). Whereas, the transducer 14b that senses the maternal contractions need not have any filtering since it is a very long period, e.g., a large impulse.

Each amplifier 14 feeds the signal to an A/D converter 44 that digitizes the signal, at a sampling frequency at least greater than twice the highest frequency component in the channel. In other implementations, a single A/D converter and a multiplexer can be used to process data from the channels (See FIG. 4). The digitized signals from each of the channels are transferred to the bus interface device 46 that formats the digitized signals to place on the bus 38 (FIG. 2) to send to the memory 34 and/or processor 32 to be processed.

Figure 4:
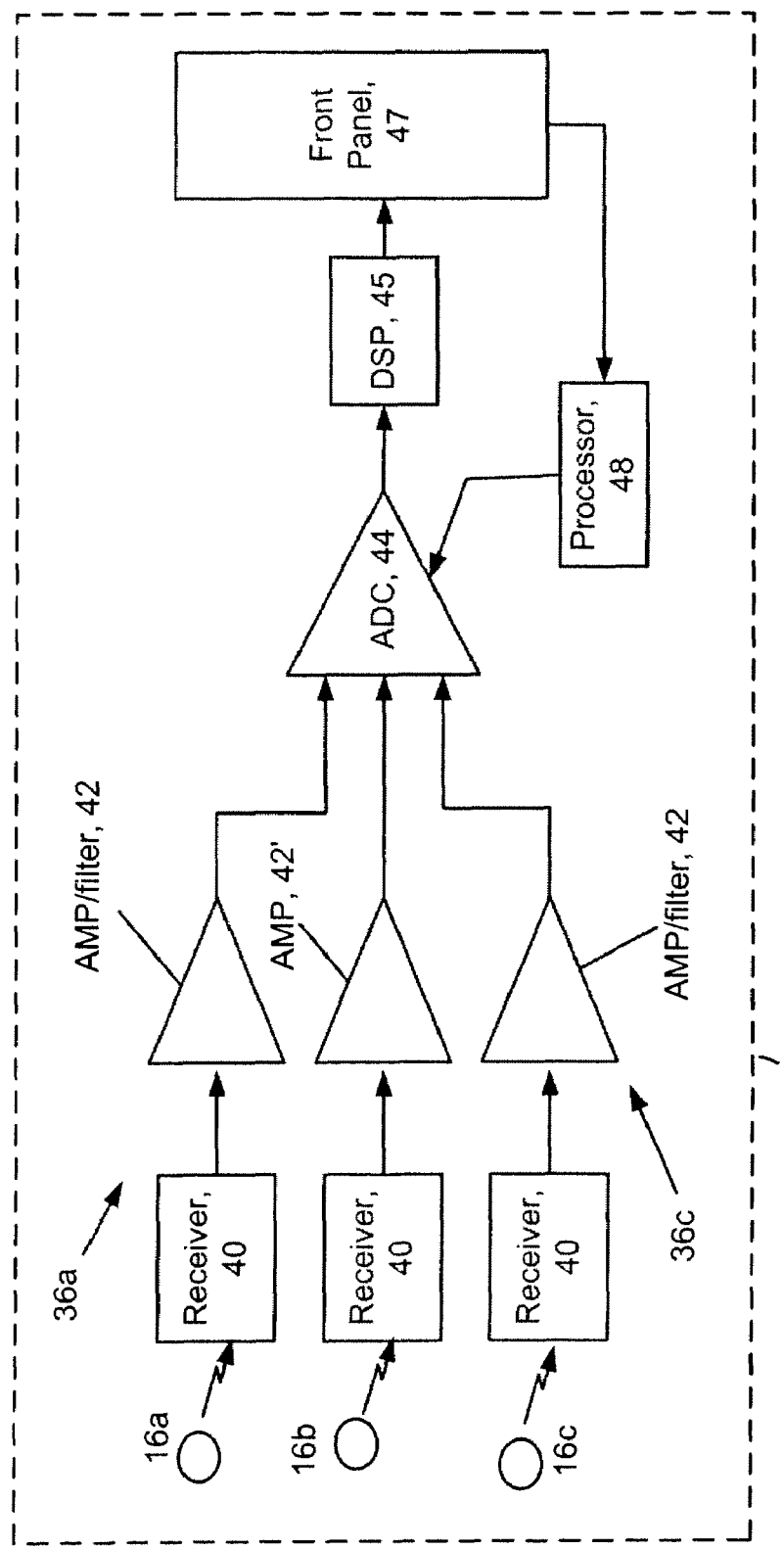
FIG. 4 is a block diagram of an alternative fetal monitor device.

Referring to FIG. 4, an alternative arrangement for the monitor 12 interfaces the monitor 12 to the transducers 16a-16c. A channel 36a-36c is provided for each transducer 16a-16c. Each channel 36a-36c includes a receiver 40 (if the monitor is a wireless version) or an analog signal interface (not shown) to cables (not shown) from the transducer, if the monitor is a wire-connected version. In addition, the interfaces 36a to 36c include a low noise amplifier and a filter generally 42 to process analog signals from the transducers 16a and 16c and a low noise amplifier generally 42' to process analog signals from the transducer 16b.

The amplifier 14 amplifies the signals and the filter filters the signals to preserve frequencies in the ranges discussed above. Each amplifier/filter 42 and amplifier 42' selectively feeds its output signal to a A/D converter/multiplexer 44 that digitizes the signal, at a sampling frequency at least greater than twice the highest frequency component in the channel, according to control provided from the processor. The single A/D converter and multiplexer 44 processes data in the selected channel and transfers the data to the digital signal processor 45 (DSP) for processing described below.

A processor 48 processes signals from a front panel to control the ADC/mux 44, whereas the DSP 45 processes output signals from the ADC/mux 44 to provide outputs to the front panel. In some implementations this can be the same device. The front panel thus includes a display, a digital readout, switches (to select which channel to process), speakers, and so forth. The monitor 10 can also include other user interface devices, e.g., keyboard or keypad, and interfaces for connection to other equipment to upload data to a server and the like.

The arrangement also includes memory, to execute programs, persistent, e.g., non-volatile storage, and I/O interface(s) all coupled via buses (not shown) to the digital signal processor 45 and processor 48.

Executed by DSP 45 is signal processing software 50 that processes signals from the transducers 16a and 16c from the pregnant woman's heart and the fetus's heart, respectively. The monitor also processes signals from the transducer 16b that monitors for contractions in the pregnant woman's uterus. This data are fed to the processor to determine contraction rates that are sent to the front panel for display.

Processing 50 provides a relatively clean detection of the fetal heartbeat by eliminating major sources of noise in the fetal heartbeat signal, e.g., the relatively strong acoustic energy components contributed to the detected fetal heartbeat caused by the pregnant woman's heartbeat. In some embodiments, acoustic energy components from uterine contractions could also be filtered from the detected fetal heartbeat acoustic energy.

Figure 5:
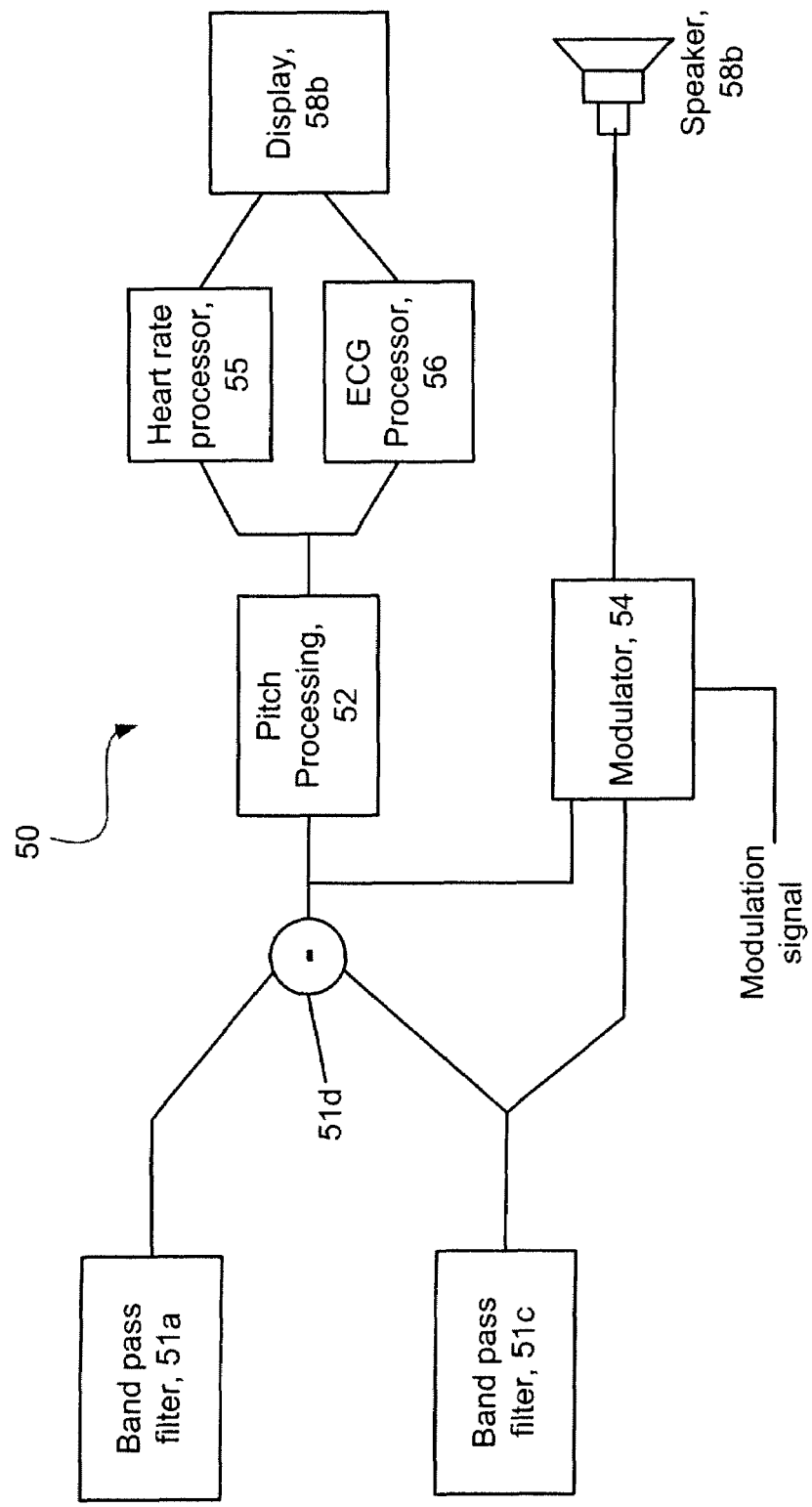
FIG. 5 is a block diagram depicting processing.

Referring to FIG. 5, processing of signals from the transducers is shown. The signals from channels 36a, 36c are passed through digital band pass filters 51a, 51b to filter the signals in the range discussed above, e.g., 18 to 25 Hz for the fetal channel and 8 to 12 Hz for the maternal channel. The other ranges above could be used. The component of the pregnant woman's heartbeat that appears in the fetal channel is removed from the fetal signal in the difference block 51c. From the difference block, the signal is fed to a pitch track processor 52. The pitch track processor 52 uses pitch tracking and a principal component analysis to generate waveforms that can be used to determine heart rates, e.g., in heart rate processor 55 and process the signal to provide an ECG from ECG processor 56. These signals can be displayed on display 58.

The modulator 54 takes the output signal from the difference block 51d and modulates it with a signal in the audible spectrum of human hearing. That is, the modulator adds a carrier to the signal from the difference block 51d to provide an output signal that can be heard by humans. This signal can be converted to an analog representation and fed to an audio amplifier, to be rendered from a speaker 58b, etc. Details of processing are discussed below.

Figure 7A:
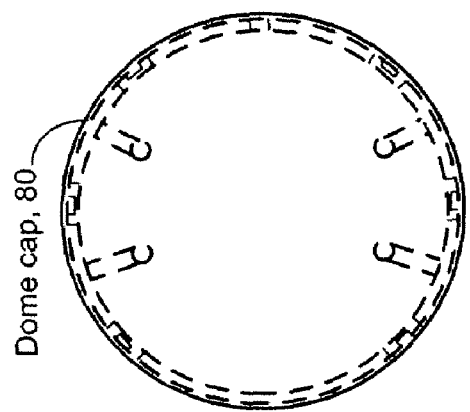
Figure 7D:
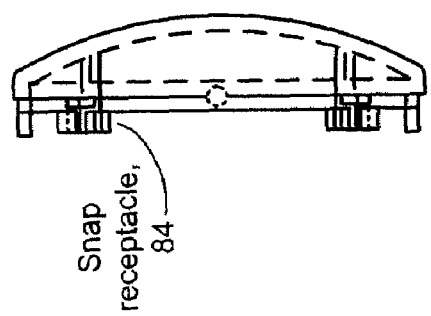
Figure 7B:
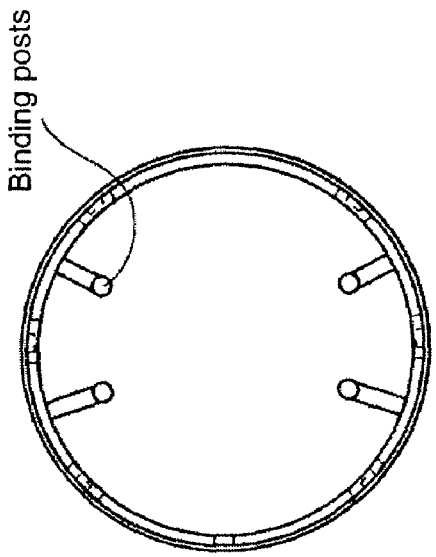
Figure 7C:
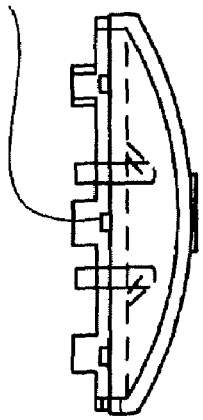
Figures 8A, 8B:
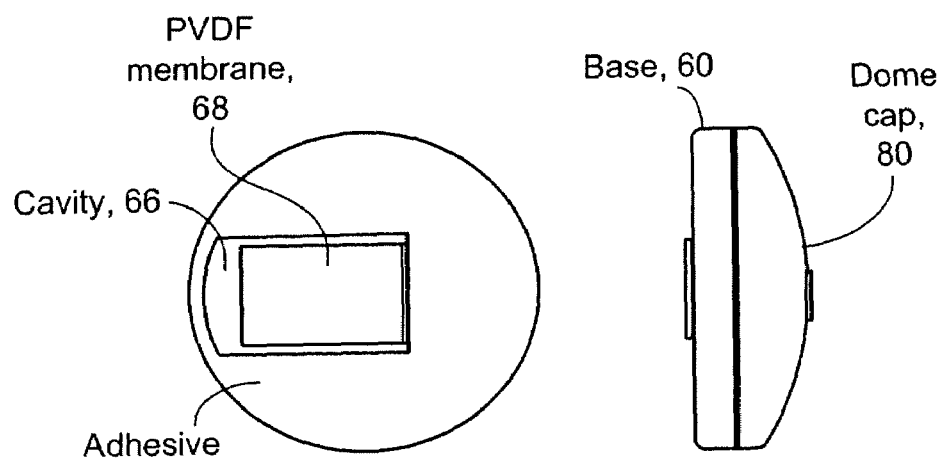
Figure 8C:
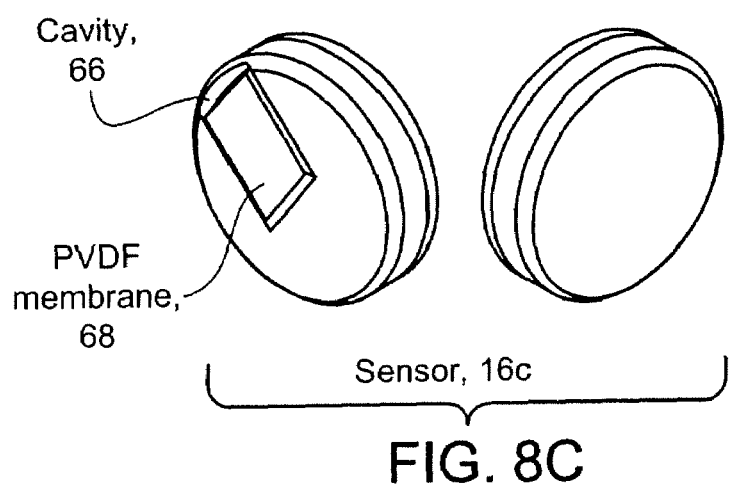

Referring to FIGS. 6A-6E through 8A-8C, collectively FIGS. 6-8, details of construction for an acoustic transducer "button" 16c transducer to acquire sound waves in the audible spectrum from the fetal heart are shown. A similar arrangement can be used for the transducer 16a to acquire the maternal heart beat signal and transducer 16b, the tocodynamometer (TOCO) transducer to detect maternal contractions, as further described below.

Transducer 16c is a relatively small, self-adhering, device that, in some implementations, is wireless. Transducer 16c is attached to the epidermis of the maternal abdomen, via a layer of an adhesive, e.g., an adhesive tape 61, in particular a double-sided adhesive, which in addition to providing for attachment of the transducer 16c to the epidermis also provides acoustic impedance matching between the epidermis and a piezoelectric membrane that detects acoustic energy in the transducer. The transducer 16c captures acoustic energy that emanates from the maternal abdomen through the uterus.

Referring to FIGS. 6A-6E, collectively, FIG. 6, the acoustic transducer "button" 16c includes a base member 60. The base member 60, as depicted in FIG. 6A, includes a frame arrangement 62 that supports bosses 64 to carry a circuit board (not shown) that supports signal preconditioning circuits, as discussed in FIG. 9.

FIG. 6A depicts an aperture 66 in a bottom portion 60a of the base 60. A polymer membrane 68 covers a substantial portion of the aperture 66a. The polymer membrane 68 is sandwiched between a pair of electrodes over the opposing major surfaces of the polymer membrane 68. A pair of wires (not shown), for example, are attached to the electrodes of the polymer 68. Bosses are provided in the base 60 to elevate a circuit board above the plane of the bottom of the base 60 to provide clearance for wires, that couple to the electrodes on the polymer membrane 68.

As shown in FIG. 6B, the polymer membrane 68 is disposed through a cavity 65 in the bottom of the base 60, such that the polymer membrane 68 rests within but is not interfered with by sides of the base 60 that form cavity 65. The cavity can be eliminated. For instance, depending on manufacturing constraints other configurations such as connecting the PCB to the membrane via electrodes provided through the base may be preferred. In addition a foam type material can occupy the cavity, e.g., the cavity can be filled with another material, e.g., an acoustic foam material. The polymer membrane 68 has a major surface that is contacted by the double-sided adhesive tape 61 on what will be the outside of the base 60, as shown in FIG. 6C, and a second major surface that is within the transducer.

The adhesive layer 61 is provided on the bottom of the base and over the outside surface of the polymer membrane 68. In general, the adhesive layer contacts the polymer membrane 68 on the outside, major surface, thus securing the polymer membrane 68 into the transducer. The adhesive 69 is provided as a double-sided adhesive medical-grade tape of a 4.5 mil double coated polyester tape, coated on both sides with a hypoallergenic, pressure sensitive synthetic rubber based adhesive on a 1 mil transparent polyester carrier, with a release liner silicone coated 60 lb bleached Kraft paper. This tape is ethylene oxide, gamma and autoclave process tolerant. One suitable product is Tape No. 9877 from 3M Corporation Minneapolis Minn. Other adhesive tapes and adhesives could be used.

In conventional approaches, as mentioned above an acoustic match is provided by a gel that is applied on the maternal abdomen. Typically, the operator covers a region of the abdomen with the gel (a slippery, non-sticky clear gel) and moves the ultrasonic sensor around the area to scan the area. Alternatively, the conventional ultrasonic sensor can be affixed with a belt that is worn around the woman. The belt is cumbersome and especially inaccurate (since often the sensor slips off of its target) and it has to be removed prior to surgery or emergency procedures.

In contrast, the adhesive tape 61 secures the polymer membrane to the transducer 16a, holding one major surface of the polymer, e.g., the outer surface of the polymer, while permitting the other major surface of the polymer 68 to be free to vibrate in the cavity 65 of the transducer. The adhesive tape 61, as discussed above, provides acoustic coupling between the polymer 68 and the maternal abdomen. In some embodiments, material can be interposed between the tape and the polymer membrane for additional acoustic impedance matching. Here the tape 69 provides acoustic impedance matching, while securing the polymer 68 to the transducer 16c and also securing the transducer 16c to the abdomen of the patient.

As depicted in FIG. 6D, a snap member 71 is disposed on an inner portion of the sidewall of the base member 60, to fasten a dome cap member 74 (FIGS. 7A-7D) to the base member 60. Here five additional snap members are disposed about the base, adjacent to the bosses, as denoted by "S." FIG. 6E shows a side view of the base member 60 from a side opposing the slot 69.

Referring to FIGS. 7A-7D, collectively FIG. 7, the dome cap member 80 is illustrated. The dome cap 80 has a generally convex outer surface, as depicted in FIG. 7A. The dome cap member supports a set of binding posts 82 that align with the base member 80 (FIG. 6) to secure the circuit board (not shown) inside the dome cap 80 and urge the circuit board against the bosses 64 on the base member 60, as depicted in FIG. 7C. The dome cap 80 has a generally convex outer surface to increase the mechanical integrity of the transducer housing.

FIGS. 7C and 7D depict details of the snap receptacle member 84 to secure the dome 80 to the base 60. Other fastening arrangements are possible including gluing, screw fastening, welding and so forth.

The base 60 and the dome 80 are comprised of a generally translucent material. One type of material for the dome 80 and base 60 is ABS, especially medically approved ABS. ABS is a plastic, especially any of a class of plastics based on acrylonitrile-butadiene-styrene copolymers. ABS has sufficient strength to support the weight of a pregnant women should she roll over onto the transducer, is medically approved, and is translucent. Other types of materials, especially plastics having sufficient strength and preferably translucence or transparency could be used.

By using a translucent (or transparent) plastic, an optical type of indicator, such as a light emitting diode (LED) can be coupled to the circuitry inside the device. One or a series of LED's can be used to indicate status and health of the transducer, as discussed below. The LED's could also be outside of or mounted into the base or dome the device.

Referring to FIGS. 8A-8D, the assembled transducer 16c is illustrated with the base member 60 secured in place to the dome cap 80, with the polymer membrane 68 exposed on the bottom with the adjacent cavity 66.

Figure 9A:
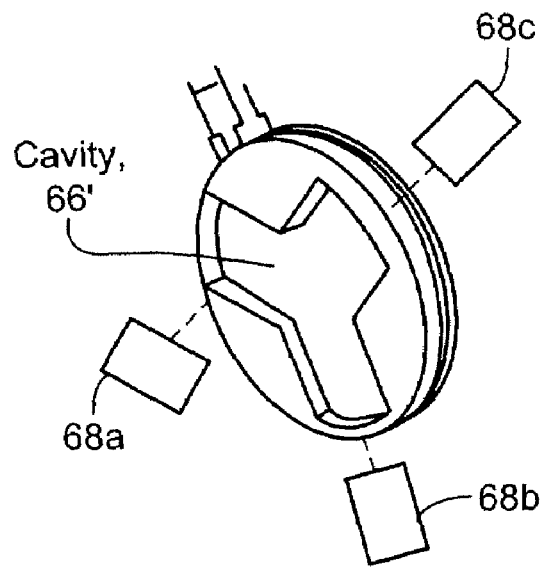
FIGS. 9A-9B (collectively FIG. 9) is a set of diagrams depicting an alternate pattern for a piezoelectric sensor element.
Figure 9B:
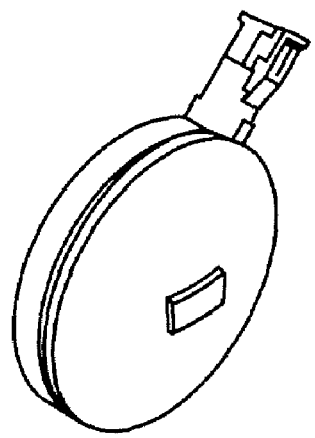

Referring to FIGS. 9A-9B, collectively FIG. 9, an alternative construction is shown. Here the base member 60' has a aperture 66' that is in a generally "Y" shape, e.g., with three rectangular aperture regions converging together, in which are disposed three (3) polymer membranes 68a-68c. The membranes 68a-68c improve sensitivity and can be electrically coupled in series to increase the overall voltage produced from the patient or in parallel to increase the amount of charge and hence reduce the input impedance for the high impedance amplifier.

The polymer membrane 68 or 68a-68c can be comprised of any suitable polymer material that exhibits piezoelectric properties. Certain polymer and copolymer materials such as polyvinyldene fluoride (PVDF) have long repeating chains of "$CH_2$—$CH_2$" molecules that when "orientated" provide a crystalline structure and a net polarization. Such a sheet of orientated material disposed between a pair of electrodes, for example, can detect mechanical energy by producing a net charge or produce mechanical energy by application of charge.

Films can be obtained from Measurement Specialties Inc. Valley Forge Pa. as part No. SDT1-028k, which is equivalent to DT1-028k whose properties are in the table below, but without a protective urethane coating. This is a 028 micron thick polymer sheet with Silver ink electrodes although NiCu-alloys could be used. Leads can be placed on separately or can be provided by the manufacturer. Leads can be attached by compressive clamping, crimps, eyelets, conductive epoxy or low temperature solders and so forth.

| Number | A Film | B electrode | C film | D electrode | E thickness | F Capacitance |
|---|---|---|---|---|---|---|
| DT1-028K | .64 (16) | .484 (12) | 1.63 (41) | 1.19 (30) | 40 | 1.38 nf |

Where dimensions A-E are in millimeters (mm), F is capacitance (nf) nanofarads and where A and C are the width and length of the film, B and D are the width and length of the electrode and E is the thickness of the PVDF polymer. Other thickness, sizes and types of piezoelectric PVDF polymer could be used.

In one mode of operation, mechanical energy in the form of acoustic energy from the pregnant woman (detected fetal and maternal heartbeats or detected contractions) impinge upon the combination of electrodes and sheet of material causing mechanical deforming of the orientated crystalline structure of the sheet. This mechanical deformation produces a voltage potential across the sheet of material, providing a potential difference between the pair of electrodes. This potential difference is amplified by the circuitry on the circuit board, is preprocessed, and transmitted to the monitor 12.

The transducer 16a for measurement of audible spectrum sound waves from the maternal heart can be constructed in a similar manner. This button will be attached to the epidermis, e.g. the precordium, and will sense acoustic waves and send the signal to the interface 36 for processing. In general, the precordium is the external surface of the body overlying the heart and stomach, typically, in the case of a pregnant woman, under the left breast of the patient.

A tocodynamometer (TOCO) transducer 16b for measurement of maternal uterine contractions is also constructed in a similar manner. The tocodynamometer (TOCO) transducer 16b like the other transducers is a self-powered device, at least in wireless applications. The tocodynamometer (TOCO) transducer 16b is a small, self-adhering device that detects contractions of the muscles of the pregnant woman's uterus by sensing tightening of the maternal epidermis in the vicinity of the uterus. Transducer 16b is similar in construction to the transducers 16a and 16c, and is coupled to the monitor 12, via one of the input channels. The signal from the transducer 16b is processed to provide a measure of the rate of contractions of the uterus.

In an alternative embodiment, the TOCO transducer 16b is a conventional strain gauge, which does not require the acoustic equipment of the heart beat monitor.

Together, transducers 16a and 16c comprise a transducer system for capturing acoustic energy that can include the fetal heart signal and with the analysis described in FIGS. 4 and 5 can produce an audible and acoustic signal of the fetal heart from which the fetal condition can be ascertained.

In addition, the transducer 16a and 16b provide a transducer system that provides signals that when processed provide an indication of the labor status of the pregnant woman, e.g., heart rate and rate of uterine contractions.

The set of transducers 16a-16c provides minimal discomfort to the pregnant woman, complete transparency with regard to the currently employed delivery room fetal monitoring techniques, and minimal and virtually no interference with emergency surgical procedures such as emergency cesarean section, especially with the wireless embodiments.

The wireless communication employed is low-power radio-frequency (RF) signals in compliance with FCC regulations posing no risk (according to contemporary medical views) to the pregnant woman, the infant, or any technicians and clinicians. One preferred wireless technology employed is low power, Bluetooth® (Bluetooth® SIG, Inc.) wireless technology approved for medical applications.

Figure 10:
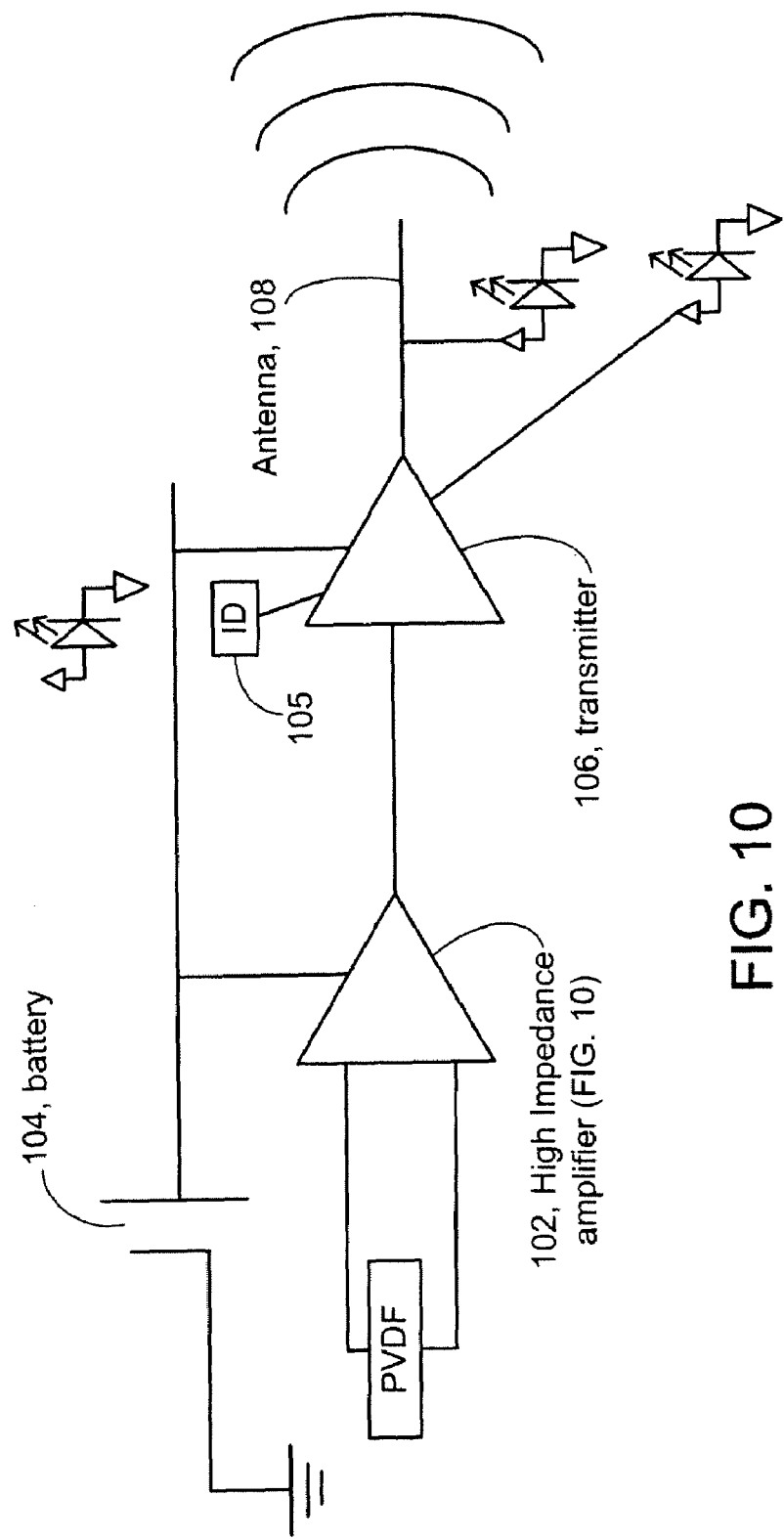
FIG. 10 is a block diagram of circuitry used in the sensors.

Referring to FIG. 10, circuitry 100 on the circuit board housed in the transducer 16c is shown. The circuitry 100 includes a high impedance amplifier 102 that interfaces to wires from the electrodes on the polymer membrane 68, as well as a battery 104 and a transmitter device 106 (or a analogy driver circuit (not shown) if the transducer 16c is coupled to the monitor 12 via wires. Also included is an antenna element 108, here a dipole antenna internal to the transducer. An on-chip antenna device may also be used. Other techniques could be used such as infrared or optical.

In a wired implementation, power to the devices could be delivered via wires that attached to the transducer, whereas in the wireless implementation power is provided by a small battery, as shown in FIG. 10.

In one wireless implementation each transducer includes a unique device identifier code 105. In operation, each transducer 16a-16c when powered up would first be registered with the monitor 12, e.g., a procedure that stores in the monitor 12 the unique identifier of the transducer that the monitor is wireless coupled to. Each time the transducer sends data to the monitor, the transducer includes the transducer identifier, so that the monitor would be certain that it is processing data from the correct transducer, registered for that monitor, and not from transducers registered with a different monitor and on a different patient.

The circuitry also includes LEDS, here three being shown that light up to indicate various statuses of the transducer. For instance, using the situation of wireless transducers, the three LEDS, one red, one yellow and one green, can be used to indicate the statuses of respectively, "failure", e.g., of a battery, as shown or by failing to receive any output signal from the transmitter; "ready but not registered" by sensing a signal from the transmitter, which would be in that case a transceiver, which would receive a signal back from the monitor indicating that it is registered with the monitor; and "working" by sensing the output the transmitter. Alternatively, the LEDs can sense outputs from the amplifier.

Figure 11:
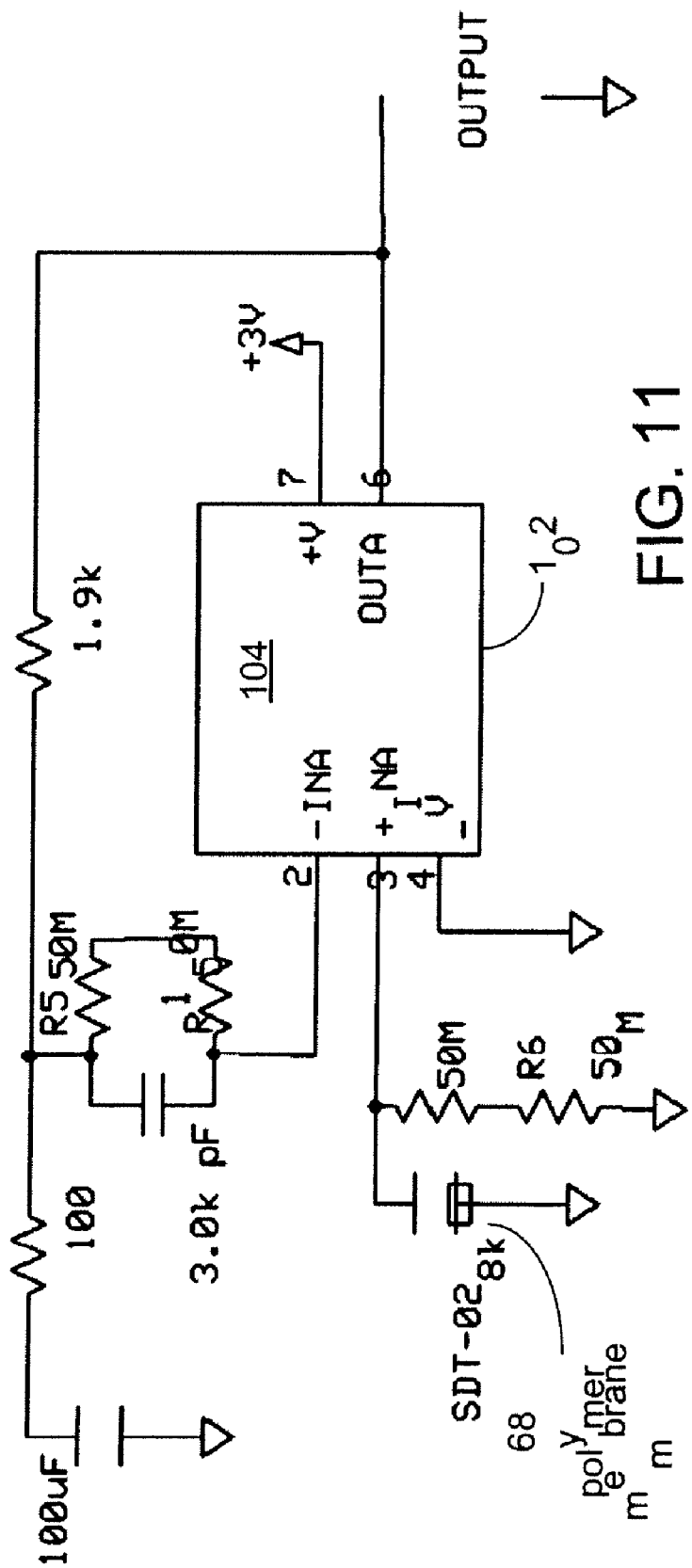
FIG. 11 is a schematic of a high impedance amplifier used with the sensors of FIGS. 6-8.

Referring to FIG. 11, the high impedance amplifier 102 is used to interface with the polymer sheet 68. Since the polymer sheet 68 is capacitive in nature, a high input impedance amplifier is used to amplify the voltage potential generated across the polymer sheet prior to transmission (either wirelessly or with wires) to the monitor. The high impedance amplifier 102 has components to set the operating point of the high impedance amplifier 102. The high impedance amplifier 102 includes an operational amplifier 104 having differential inputs one of which receives a portion of the output signal fed back to the inverting input −INA of the amplifier 104. The signal from the sheet 68 is fed to the non-inverting input +INA.

Figure 12:
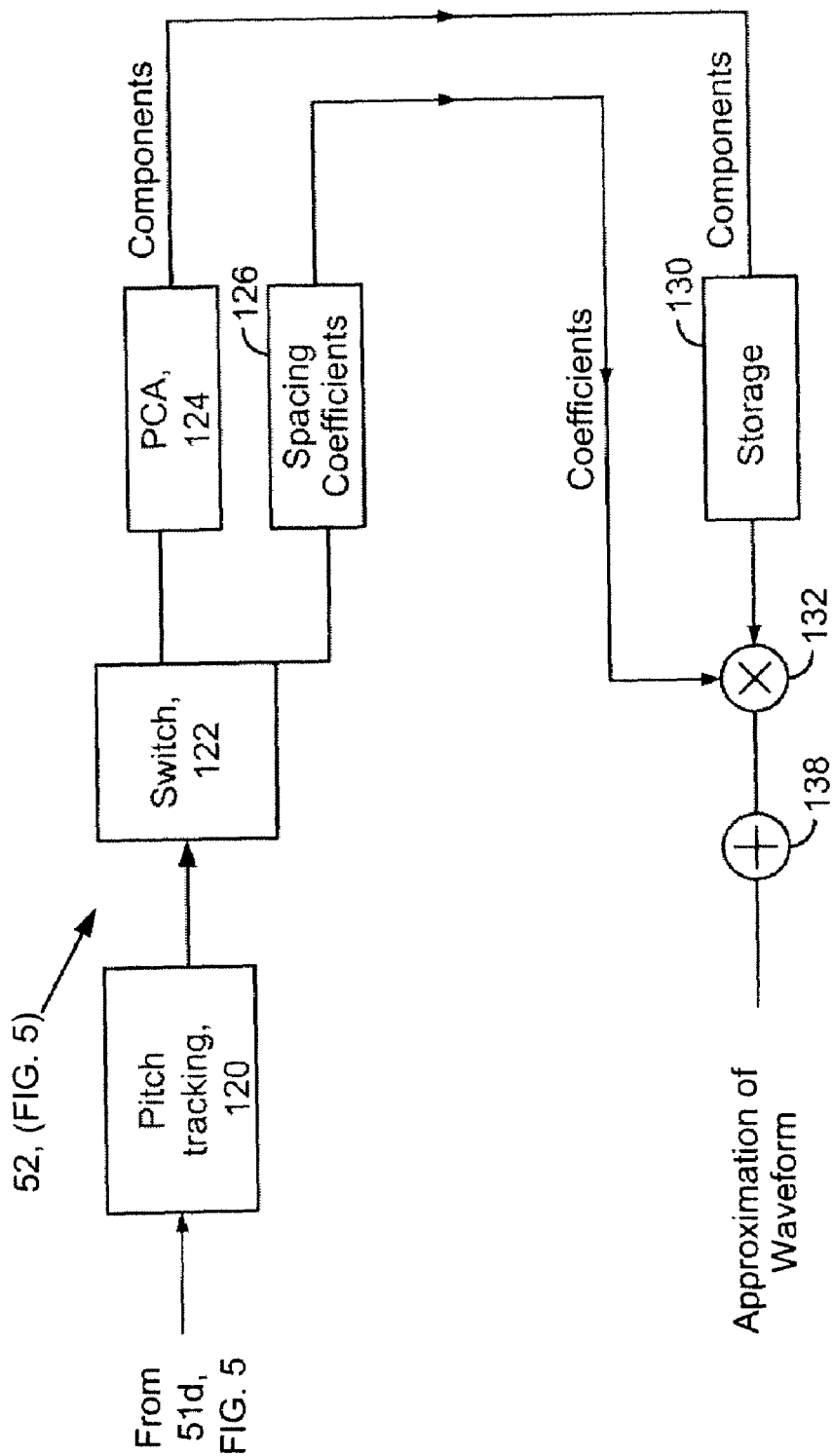
FIG. 12 is a block diagram depicting details of pitch processing

Referring now to FIG. 12, details of the pitch processing block 52 are shown. From the difference block, 51d (FIG. 5) the signal is fed to pitch track analyzer 120, a switch 122, a principal component analysis (PCA) generator 124 and a spacing coefficient generator 126.

Principal component analysis (PCA) is a linear algebraic transform. PCA is used to determine the most efficient orthogonal basis for a given set of data. When determining the most efficient axes, or principal components of a set of data using PCA, a strength (i.e., an importance value called herein as a coefficient) is assigned to each principal component of the data set.

The pitch track analyzer 120 determines the pitch periods of the input waveform. The signal switch 122 routes the signal to the PCA generator 124 during an initial calibration period. PCA generator 124 calculates the principal components for the initial pitch period received. PCA Generator 124 sends the first, e.g., 6 principal components for storage 130 and/or further processing. After the initial period, switch 122 routes the signal from the difference block to coefficient generator 126, which generates coefficients for each subsequent pitch period. Instead of sending the principal components, only the coefficients are sent, thus reducing the number of bits.

Switch 16 includes a mechanism that determines if the coefficients being used are valid. Coefficients deviating from the original coefficients by more than a predetermined value are rejected and new principal components and hence new coefficients are determined.

The pitch tracking analyzer 120 and the other components mention above are described in U.S. patent application Ser. No. 10/624,139 filed Jul. 21, 2003, published US-2004-0102965-A1 May 27, 2004 by Ezra J. Rapoport incorporated herein by reference in its entirety.

The pitch track analyzer 120 determines the pitch periods of the input waveform. The pitch track analyzer 120 determines trends in the slight changes that modify a waveform across its pitch periods including quasi-periodic waveforms like heartbeat signals. In order to analyze the changes that occur from one pitch period to the next, a waveform is divided into its pitch periods using pitch tracking process 53 (FIG. 13).

Figure 13:
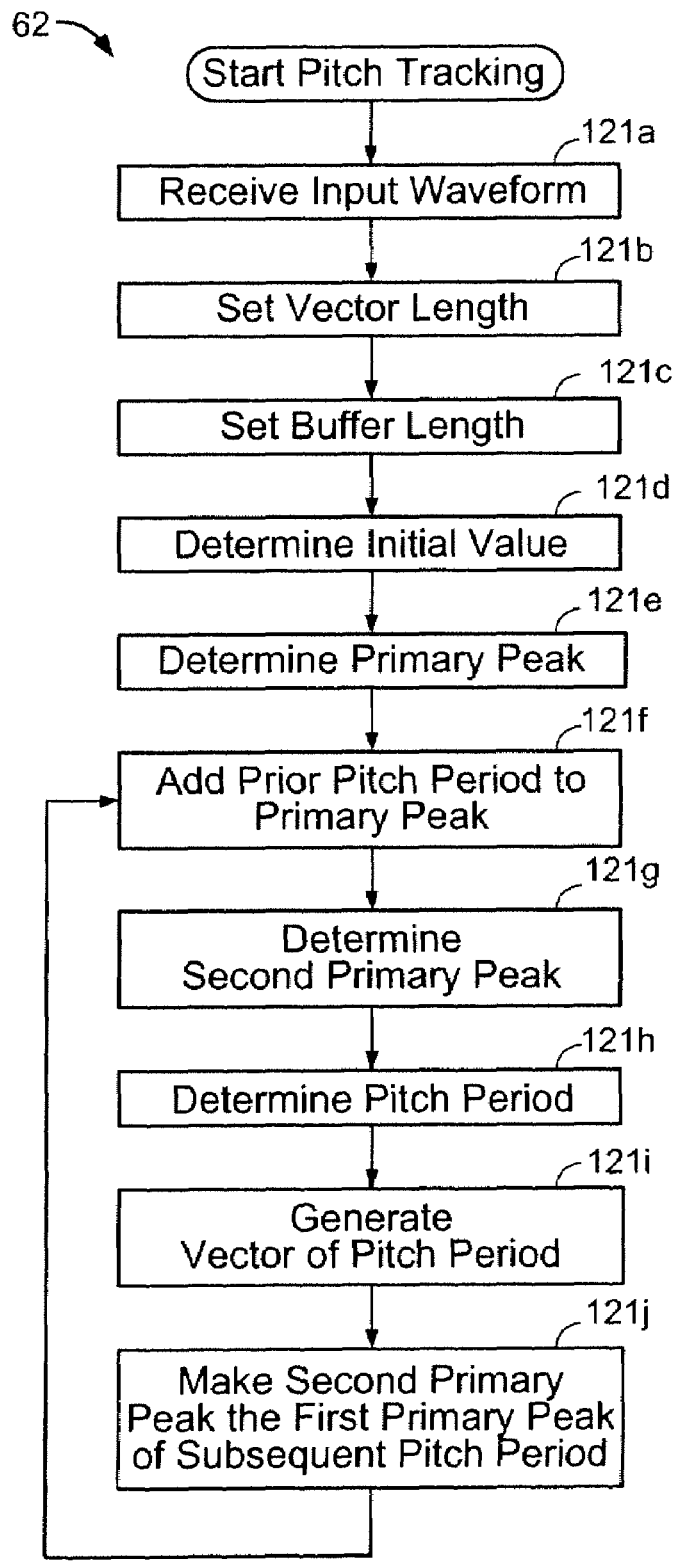
FIG. 13 is a flow chart depicting pitch processing.
Figure 14A:
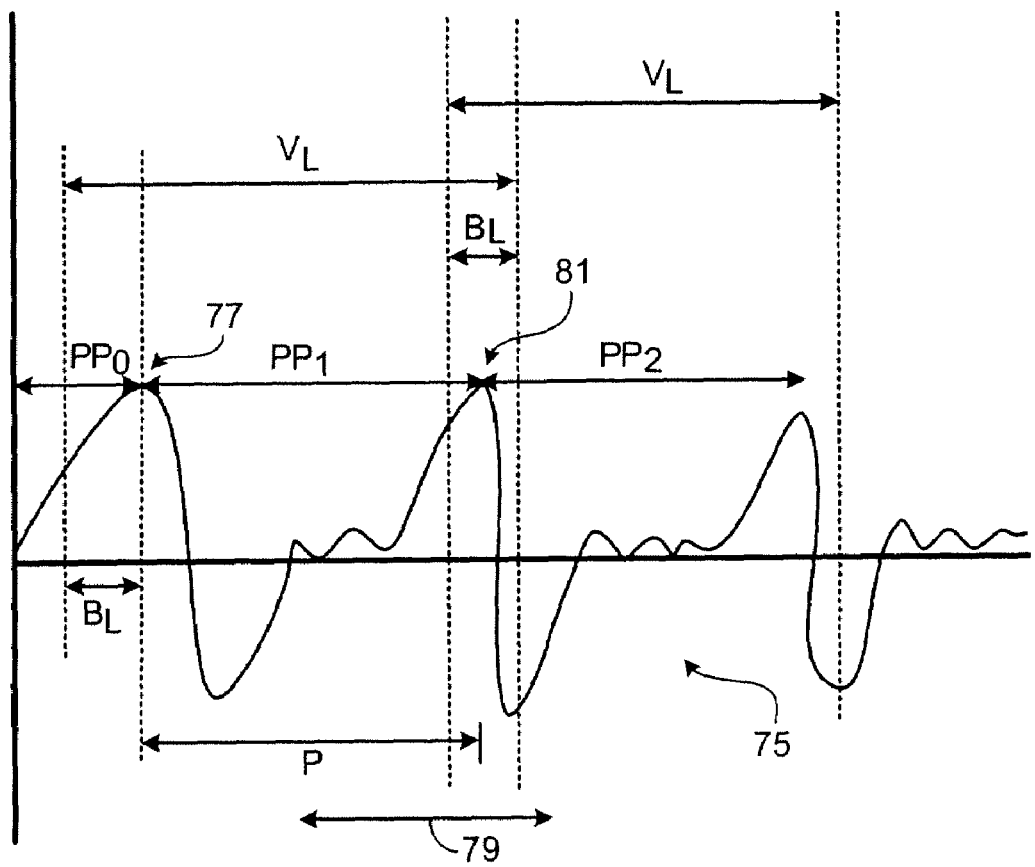
FIGS. 14A and 14B are diagrams useful in understanding processing of fetal and maternal heartbeat signals.

Referring now also to FIG. 13 a pitch tracking process 121 receives 121a an input waveform 75 (FIG. 14A) from difference block 51c to determine the pitch periods. Even though the waveforms of fetal heartbeat are quasi-periodic, a fetal heartbeat still has a pattern that repeats for the duration of the input waveform 75. However, each iteration of the pattern, or "pitch period" (e.g., $PP_1$) varies slightly from its adjacent pitch periods, e.g., $PP_0$ and $PP_2$. Thus, the waveforms of the pitch periods are similar, but not identical, thus making the time duration for each pitch period unique.

Since the pitch periods in a waveform vary in time duration, the number of sampling points in each pitch period generally differs and thus the number of dimensions required for each vectorized pitch period also differs. To adjust for this inconsistency, pitch tracking analyzer 120 designates 121b a standard vector (time) length, $V_L$. After pitch tracking process 121 executes, the pitch tracking analyzer 120 chooses the vector length to be the average pitch period length plus a constant, e.g., 40 sampling points. This allows for an average buffer of 20 sampling points on either side of a vector. The result is that all vectors are a uniform length and can be considered members of the same vector space. Thus, vectors are returned where each vector has the same length and each vector includes a pitch period.

Pitch tracking process 121 also designates 121c a buffer (time) length, $B_L$, which serves as an offset and allows the vectors of those pitch periods that are shorter than the vector length to run over and include sampling points from the next pitch period. As a result, each vector returned has a buffer region of extra information at the end. This larger sample window allows for more accurate principal component calculations (discussed below). In the interest of storage reduction, the buffer length may be kept to between 10 and 20 sampling points (vector elements) beyond the length of the longest pitch period in the waveform.

At 8 kHz, a vector length that includes 120 sample points and an offset that includes 20 sampling units can provide optimum results.

Pitch tracking process 121 relies on the knowledge of the prior period duration, and does not determine the duration of the first period in a sample directly. Therefore, pitch tracking process 121 determines 121d an initial period length value by finding a real "cepstrum" of the first few pitch periods of the heartbeat signal to determine the frequency of the signal. A cepstrum is an anagram of the word "spectrum" and is a mathematical function that is the inverse Fourier transform of the logarithm of the power spectrum of a signal. The cepstrum method is a standard method for estimating the fundamental frequency (and therefore period length) of a signal with fluctuating pitch.

A pitch period can begin at any point along a waveform, provided it ends at a corresponding point. Pitch tracking process 121 considers the starting point of each pitch period to be the primary peak or highest peak of the pitch period.

Pitch tracking process 121 determines 121e the first primary peak 77. Pitch tracking process 121 determines a single peak by taking the input waveform, sampling the input waveform, taking the slope between each sample point and taking the point sampling point closest to zero. Pitch tracking process 121 searches several peaks within an expectation range and takes the peak with the largest magnitude as the subsequent primary peak 77. Pitch tracking process 121 adds 121f the prior pitch period to the primary peak. Pitch tracking process 121 determines 121g a second primary peak 81 locating a maximum peak from a series of peaks 79 centered a time period, P, (equal to the prior pitch period, $PP_0$) from the first primary peak 77. The peak whose time duration from the primary peak 77 is closest to the time duration of the prior pitch period $PP_0$ is determined to be the ending point of that period ($PP_1$) and the starting point of the next ($PP_1$). The second primary peak is determined by analyzing three peaks before or three peaks after the prior pitch period from the primary peak and designating the largest peak of those peaks as the second peak 82.

Process 121 vectorizes 121i the pitch period. Pitch tracking processor 120 makes 121j the second primary peak the first primary peak of the next pitch period and recursively executes, e.g., back to 121f, returning a set of vectors. That is, pitch tracking process 120 designates 121j the second primary peak as the first primary peak of the subsequent pitch period and reiterates (121f)-(121j).

Each set of vectors corresponds to a vectorized pitch period of the waveform. A pitch period is vectorized by sampling the waveform over that period, and assigning the $i^{th}$ sample value to the $i^{th}$ coordinate of a vector in Euclidean n-dimensional space, denoted by $\Re^n$, where the index i runs from 1 to n, the number of samples per period. Each of these vectors is considered a point in the space $\Re^n$.

Figure 14B:
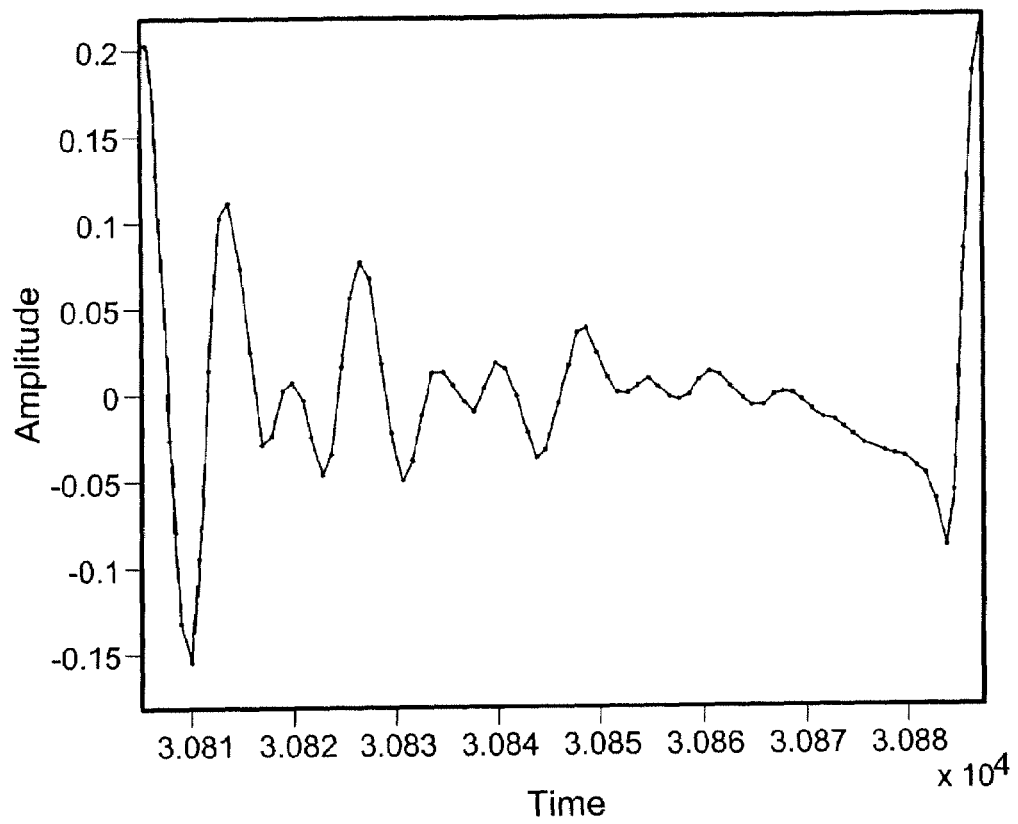

FIG. 14B shows an illustrative sampled waveform of a pitch period. The pitch period includes 82 sampling points (denoted by the dots lying on the waveform) and thus when the pitch period is vectorized, the pitch period can be represented as a single point in an 82 (or higher)—dimensional space.

Thus, pitch tracking processor 120 identifies the beginning point and ending point of each pitch period. Pitch tracking processor 120 also accounts for the variation of time between pitch periods. This temporal variance occurs over relatively long periods of time and thus there are no radical changes in pitch period length from one pitch period to the next. This allows pitch tracking process 62 to operate recursively, using the length of the prior period as an input to determine the duration of the next.

Pitch tracking processor 120 can be stated as the following recursive function:

$$f(p_{prev}, p_{new}) = \begin{cases} f(p_{new}, p_{next}) : |s - d(p_{new}, p_0)| \le |s - d(p_{prev}, p_0)| \\ d(p_{new}, p_0) : |s - d(p_{new}, p_0)| > |s - d(p_{prev}, p_0)| \end{cases}$$

The function $f(p,p')$ operates on pairs of consecutive peaks p and p' in a waveform, recurring to its previous value (the duration of the previous pitch period) until it finds the peak whose location in the waveform corresponds best to that of the first peak in the waveform. This peak becomes the first peak in the next pitch period. In the notation used here, the letter p subscripted, respectively, by "prev," "new," "next" and "0," denote the previous, the current peak being examined, the next peak being examined, and the first peak in the pitch period respectively. The value "s" denotes the time duration of the prior pitch period, and d(pp') denotes the duration between the peaks p and p'.

B. Principal Component Analysis

Principal component analysis is a method of calculating an orthogonal basis for a given set of data points that defines a space in which any variations in the data are completely uncorrelated. PCA can be used as a compression technique to store pitch periods from the pitch tracking processor for detailed analysis. The symbol, "$\Re^n$" is defined by a set of n coordinate axes, each describing a dimension or a potential for variation in the data. Thus, n coordinates are required to describe the position of any point. Each coordinate is a scaling coefficient along the corresponding axis, indicating the amount of variation along that axis that the point possesses. An advantage of PCA is that a trend appearing to span multiple dimensions in $\Re^n$ can be decomposed into its "principal components," i.e., the set of eigen-axes that most naturally describe the underlying data. By implementing PCA, it is possible to effectively reduce the number of dimensions. Thus, the total amount of information required to describe a data set is reduced by using a single axis to express several correlated variations.

For example, FIG. 6A shows a graph of data points in 3-dimensions. The data in FIG. 6B are grouped together forming trends. FIG. 6B shows the principal components of the data in FIG. 6A. FIG. 6C shows the data redrawn in the space determined by the orthogonal principal components. There is no visible trend in the data in FIG. 6C as opposed to FIGS. 6A and 6B. In this example, the dimensionality of the data was not reduced because of the low-dimensionality of the original data. For data in higher dimensions, removing the trends in the data reduces the data's dimensionality by a factor of between 20 and 30 in routine speech applications. Thus, the purpose of using PCA in this method of compressing speech is to describe the trends in the pitch-periods and to reduce the amount of data required to describe speech waveforms.

Figure 15:
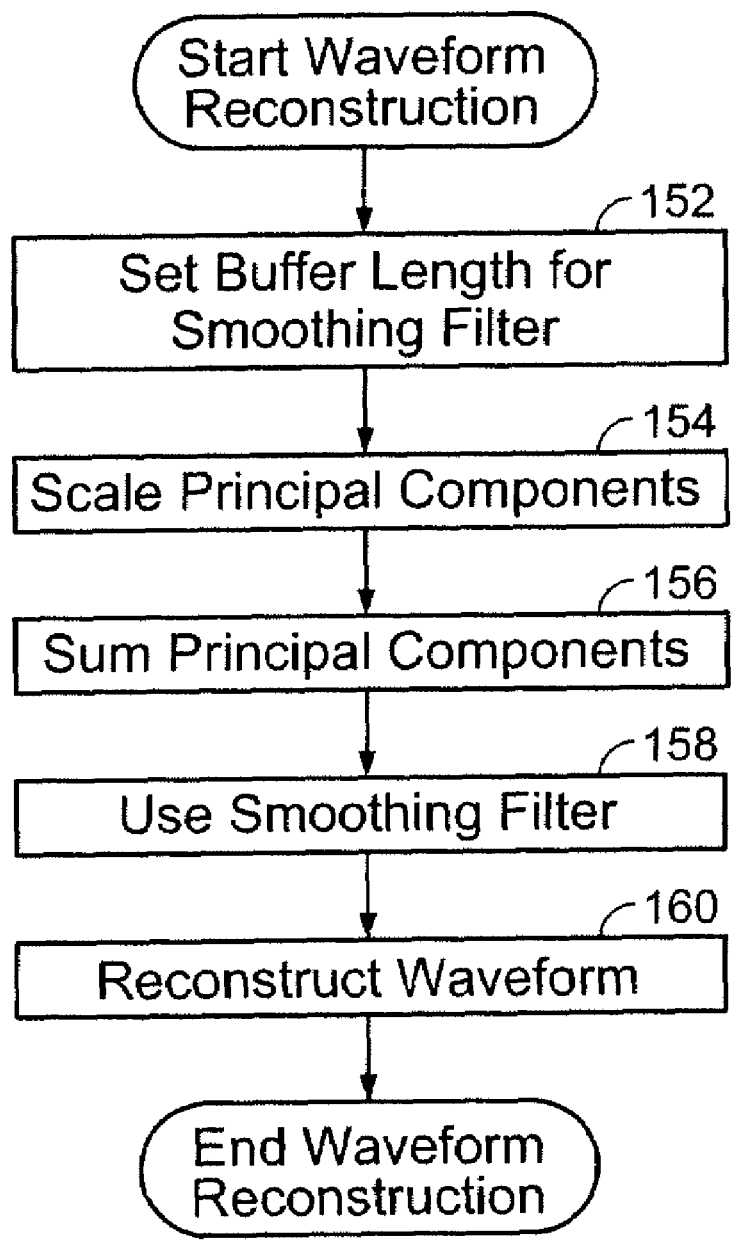
FIG. 15 is a flow chart depicting principal component analysis.

Referring to FIG. 15, principal components process 124 determines (152) the number of pitch periods generated from pitch tracking process 121. Principal components process 124 generates (154) a correlation matrix.

The actual computation of the principal components of a waveform is a well-defined mathematical operation, and can be understood as follows. Given two vectors x and y, $xy^T$ is the square matrix obtained by multiplying x by the transpose of y. Each entry $[xy^T]_{i,j}$ is the product of the coordinates $x_i$ and $y_j$. Similarly, if X and Y are matrices whose rows are the vectors $x_i$ and $y_j$, respectively, the square matrix $XY^T$ is a sum of matrices of the form $[xy^T]_{i,j}$:

$$XY^T = \sum_{i,j} x_i y_j^T.$$

$XY^T$ can therefore be interpreted as an array of correlation values between the entries in the sets of vectors arranged in X and Y. So when X=Y, $XX^T$ is an "autocorrelation matrix," in which each entry $[XX^T]_{i,j}$ gives the average correlation (a measure of similarity) between the vectors $x_i$ and $x_j$. The eigenvectors of this matrix therefore define a set of axes in $\Re^n$ corresponding to the correlations between the vectors in X. The eigen-basis is the most natural basis in which to represent the data, because its orthogonality implies that coordinates along different axes are uncorrelated, and therefore represent variation of different characteristics in the underlying data.

Principal components process 124 determines (156) the principal components from the eigenvalue associated with each eigenvector. Each eigenvalue measures the relative importance of the different characteristics in the underlying data. Process 124 sorts (158) the eigenvectors in order of decreasing eigenvalue, in order to select the several most important eigen-axes or "principal components" of the data.

Principal components process 124 determines (160) the coefficients for each pitch period. The coordinates of each pitch period in the new space are defined by the principal components. These coordinates correspond to a projection of each pitch period onto the principal components. Intuitively, any pitch period can be described by scaling each principal component axis by the corresponding coefficient for the given pitch period, followed by performing a summation of these scaled vectors. Mathematically, the projections of each vectorized pitch period onto the principal components are obtained by vector inner products:

$$x' = \sum_{i=1}^{n} (e_i \cdot x) e_i.$$

In this notation, the vectors x and x' denote a vectorized pitch period in its initial and PCA representations, respectively. The vectors $e_i$ are the ith principal components, and the inner product $e_i \cdot x$ is the scaling factor associated with the ith principal component.

Therefore, if any pitch period can be described simply by the scaling and summing the principal components of the given set of pitch periods, then the principal components and the coordinates of each period in the new space are all that is needed to reconstruct any pitch period and thus the principal components and coefficients are the compressed form of the original heartbeat signal. In order to reconstruct any pitch period of n sampling points, n principal components are necessary.

In the present case, the principal components are the eigenvectors of the matrix $SS^T$, where the ith row of the matrix S is the vectorized ith pitch period in a waveform. Usually the first 5 percent of the principal components can be used to reconstruct the data and provide greater than 97 percent accuracy. This is a general property of quasi-periodic data. Thus, the present method can be used to find patterns that underlie quasi-periodic data, while providing a concise technique to represent such data. By using a single principal component to express correlated variations in the data, the dimensionality of the pitch periods is greatly reduced. Because of the patterns that underlie the quasi-periodicity, the number of orthogonal vectors required to closely approximate any waveform is much smaller than is apparently necessary to record the waveform verbatim.

Another type of analysis is the complex wavelet transform, as described in *Dual-Tree Complex Wavelet Transform*, Ivan W. Selesnick, et al., IEEE Signal Processing Magazine 123 November 2005, which is incorporated herein in its entirety.

The invention can be implemented in digital electronic circuitry, or in computer hardware, firmware, software, or in combinations thereof. Apparatus of the invention can be implemented in a computer program product tangibly embodied in a machine-readable storage device for execution by a programmable processor; and method actions can be performed by a programmable processor executing a program of instructions to perform functions of the invention by operating on input data and generating output.

The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD_ROM disks. Any of the foregoing can be supplemented by, or incorporated in, ASICs (application-specific integrated circuits).

A number of embodiments of the invention have been described. Other embodiments are within the scope of the following claims. Thus, it will be understood that various modifications may be made without departing from the spirit and scope of the invention.

What is claimed is:

1. A method of monitoring first and second acoustic signals generated by a subject, the method comprising:
    adhering at least one acoustic transducer to an epidermis of the subject, the acoustic transducer configured to be acoustically coupled directly to the epidermis of the subject via an adhesive layer;
    receiving from said at least one acoustic transducer at least one electrical signal representative of said first and second acoustic signals generated by the subject;
    digitally filtering said at least one electrical signal to distinguish a first set of frequencies associated with the first acoustic signal from a second set of frequencies associated with the second acoustic signal; and
    obtaining an electrical signal based on said first set of frequencies, said electrical signal representative of the first acoustic signal.

2. The method of claim 1, wherein the at least one acoustic transducer comprises a plurality of piezoelectric polymeric films.

3. The method of claim 1, wherein the at least one acoustic transducer comprises first and second acoustic transducers.

4. The method of claim 3, further comprising adhering the first acoustic transducer to a first region of the epidermis of the subject, and adhering the second acoustic transducer to a second region of the epidermis of the subject.

5. The method of claim 4, wherein the first region comprises an abdominal region of the subject and the second region comprises a precordial region of the subject.

6. The method of claim 3, wherein the first acoustic transducer generates a first electrical signal representative of both the first and second acoustic signals, and the second acoustic transducer generates a second electrical signal representative primarily of the second acoustic signal.

7. The method of claim 6, further comprising, after the step of digitally filtering, inputting the first and second electrical signals to a function, the output of which function comprises the electrical signal representative of the first acoustic signal.

8. The method of claim 1, wherein the first acoustic signal comprises a fetal heartbeat and the second acoustic signal comprises a maternal heartbeat.

9. The method of claim 8, further comprising monitoring a signal comprising uterine contractions.

10. The method of claim 1, wherein the at least one acoustic transducer comprises a rounded plastic housing.

11. The method of claim 1, further comprising discarding the piezoelectric polymeric film after generating the electrical signal representative of the first acoustic signal.

12. The method of claim 1, wherein the first set of frequencies is in the range of 20-30 Hz, and the second set of frequencies is in the range of 6-14 Hz.

13. The method of claim 1, wherein the first set and second sets of frequencies are each is in the range of 0.05 to 100 Hz.

14. The method of claim 1, further comprising at Least one of generating an audible tone representative of the first acoustic signal and displaying a visible waveform representative of the first acoustic signal.

15. The method of claim 1, further comprising transmitting from the acoustic transducer to a processor said at least one electrical signal representative of said first and second acoustic signals generated by the subject.

16. The method of claim 15, wherein said processor performs the steps of digital filtering said at least one electrical signal and obtaining said electrical signal representative of the first acoustic signal.

17. The method of claim 15, wherein said transmitting is performed wirelessly or via a cable.

18. The method of claim 1, wherein the piezoelectric polymeric film comprises polyvinylidene fluoride (PVDF) or a copolymer thereof.

19. The method of claim 1, wherein said obtaining comprises performing a principle component analysis of at least one of said first set of frequencies and said second set of frequencies.

* * * * *